United States Patent [19]

Clarke

[11] Patent Number: 5,053,033
[45] Date of Patent: Oct. 1, 1991

[54] INHIBITION OF RESTENOSIS BY ULTRAVIOLET RADIATION

[75] Inventor: Richard H. Clarke, Scituate, Mass.

[73] Assignee: Boston Advanced Technologies, Inc., Boston, Mass.

[21] Appl. No.: 595,033

[22] Filed: Oct. 10, 1990

[51] Int. Cl.⁵ .............................................. A61N 5/00
[52] U.S. Cl. ........................................ 606/3; 606/7; 606/15; 606/16; 128/398
[58] Field of Search .................. 606/2, 3, 7, 8, 10–16; 128/395–398; 219/121.6–121.62

[56] References Cited

U.S. PATENT DOCUMENTS

| | | | |
|---|---|---|---|
| 4,641,912 | 2/1987 | Goldenberg | 350/96.10 |
| 4,657,014 | 4/1987 | Edelman et al. | 606/15 |
| 4,732,148 | 3/1988 | L'Esperance, Jr. | 606/5 |
| 4,754,752 | 7/1988 | Ginsburg et al. | 128/303.12 |
| 4,784,132 | 11/1988 | Fox et al. | 128/303.1 |
| 4,784,135 | 11/1988 | Blum et al. | 128/303.1 |
| 4,799,479 | 1/1989 | Spears | 128/303.1 |
| 4,800,876 | 1/1989 | Fox et al. | 128/303.1 |
| 4,848,336 | 7/1989 | Fox et al. | 606/7 |
| 4,848,336 | 7/1989 | Fox et al. | 128/303.1 |
| 4,854,315 | 8/1989 | Stack et al. | 128/303.1 |
| 4,862,886 | 9/1989 | Clarke et al. | 128/303.1 |
| 4,878,492 | 11/1989 | Sinofsky et al. | 128/303.1 |
| 4,905,689 | 3/1990 | Stack et al. | 606.3/128 |

FOREIGN PATENT DOCUMENTS 0152766 8/1985 European Pat. Off. .
3502331 8/1985 Fed. Rep. of Germany .

OTHER PUBLICATIONS

Kochevar, Cytotoxicity and Mutagenicity of Excimer Laser Radiation, vol. 9, *Lasers in Surgery and Medicine*, pp. 440–445 (1989).
Green et al., Cytotoxicity and Mutagenicity of Low Intensity, vol. 47, *Cancer Research*, pp. 410–413 (1987).
Liu et al., Restenosis After Coronary Angioplasty, vol. 79, *Circulation*, pp. 1374–1387 (1989).

Primary Examiner—Stephen C. Pellegrino
Assistant Examiner—Steven J. Shumaker
Attorney, Agent, or Firm—Thomas J. Engellenner

[57] ABSTRACT

Restenosis following angioplasty can be inhibited by reducing the proliferation of smooth muscle cells in the blood vessel walls at an angioplasty site, and such reduction in cell proliferation can be accomplished by irradiating the angioplasty site with radiation in the ultraviolet (UV) wavelength range. The ultraviolet radiation is preferably delivered via an optical fiber or other waveguide incorporated, for example, into a percutaneous catheter. In operation, the ultraviolet radiation kills smooth muscle cells at the site, thereby reducing the risk of restenosis, while minimizing damage to surrounding tissue.

6 Claims, 4 Drawing Sheets

INHIBITION OF RESTENOSIS BY ULTRAVIOLET RADIATION

BACKGROUND OF THE INVENTION

The technical field of this invention is surgical instruments and procedures and, in particular, systems and methods for inhibiting restenosis associated with angioplasty.

Atherosclerosis is a disease which causes thickening and hardening of the arteries, characterized by lesions of raised fibrous plaque formed within the arterial lumen. Atherosclerotic plaque is commonly treated by means of angioplasty through the use of a balloon catheter. Balloon angioplasty involves passing a small, balloon-tipped catheter percutaneously into an artery and up to the region of obstruction. The balloon is then inflated to dilate the area of obstruction. Other devices, such as atherosclerectomy instruments which remove obstructions by dealing or shaving plaque from the artery wall, are also utilized in the treatment of atherosclerosis. More recently, laser systems have been proposed for performing angioplasty. In laser angioplasty, a catheter carrying a fiber optic waveguide is passed through a blood vessel, positioned near an obstruction, and then activated to decompose the plaque with laser radiation.

At present, over 200,000 angioplasty procedures are performed each year in the United States. Unfortunately, restenosis, or closure of the blood vessel following angioplasty, is a common occurrence following all types of such surgery. Approximately 30% of segments dilated by means of balloon catheter will develop significant restenosis, with peak incidence occurring between 2 and 3 months after angioplasty. Similar restenosis rates accompany laser angioplasty. When restenosis occurs, further coronary difficulties can result including strokes, arrhythmia, infarcts and even death.

Evidence suggests that intimal hyperplasia or proliferation of smooth muscle cells is a major factor in restenosis. proliferation of smooth muscle cells is very common in patients after angioplasty, whether or not restenosis occurs. Medial smooth muscle cells, a main component of the arterial wall, proliferate in response to any injury to the arterial wall. Smooth muscle cells enter their growth cycle between 2 and 3 days after injury, and the majority of smooth muscle cells will cease to proliferate within 7 days. The total number of smooth muscle cells in the intima reaches a peak about two weeks after injury and remains constant for up to one year, suggesting that a reduction of the number of smooth muscle cells injured during angioplasty will reduce the likelihood of subsequent restenosis. See, generally, Liu et al., "Restenosis After Coronary Angioplasty, Potential Biologic Determinants and Role of Intimal Hyperplasia," Vol. 79, *Circulation*, pp. 1374–1387 (1989).

At present, efforts to prevent restenosis typically consists of drug therapy or modification of angioplasty techniques. Drug therapy is primarily directed toward the control of restenosis through the use of antiplatelet agents, antiproliferative agents, or antimigratory agents. The goal of drug therapY is to reduce smooth muscle cell proliferation by attacking the smooth muscle cells directly, or by affecting processes that promote smooth muscle cell proliferation. Unfortunately, most of the drugs under investigation are unproven, with unknown efficiency and side effects.

An alternative approach to reduce restenosis is to modify the techniques used in performing angioplasty. Until recently, angioplasty was performed by passing a small, balloon-tipped catheter percutaneously to an obstruction site and then inflating the balloon to dilate the area of obstruction. In balloon angioplasty, the outward compression of the balloon stresses the vessel walls, often resulting in cracking or tearing of the wall and injury to the smooth muscle cells. This injury, in turn, increases the risk of restenosis. One method to reduce restenosis resulting from balloon angioplasty is to heat the balloon during dilation to "seal" the injured vessel wall. See, for example, U.S. Pat. No. 4,754,752 issued to Ginsberg et al. on July 5, 1988.

Modified forms of laser angioplasty have also been proposed to remove atherosclerotic obstructions. Up until recently, researchers in laser angioplasty primarily have relied upon continuous wave (CW) lasers. Such lasers, while sufficient to ablate an obstruction, can also substantially cause thermal injury to vessel walls adjacent to the obstruction. Recently, high energy excimer lasers and other pulsed laser sources, which possess high peak intensity levels and very rapid pulse rates, have been found to destroy the target obstruction while minimizing the thermal injury to surrounding tissue.

Nonetheless, even with these less traumatic procedures, restenosis continues to be a significant factor compromising the effectiveness of angioplasty.

There exists a need for better methods and devices for preventing restenosis after angioplasty. A system which could perform angioplasty, while reducing the likelihood of smooth muscle cell proliferation in the vicinity of the angioplasty site, would satisfy a significant need in the art.

SUMMARY OF THE INVENTION

Restenosis following angioplasty can be inhibited by reducing the proliferation of smooth muscle cells in the blood vessel walls at an angioplasty site, and such reduction in cell proliferation can be accomplished by irradiating the angioplasty site with the appropriate radiation in the ultraviolet (UV) wavelength range. The ultraviolet radiation is preferably delivered via an optical fiber or other waveguide incorporated, for example, into a percutaneous catheter. In operation, the ultraviolet radiation kills smooth muscle cells at the site, thereby reducing the risk of restenosis, while minimizing damage to surrounding tissue.

Various UV radiation sources can be use in accordance with the present invention to deliver restenosis-preventive therapy, including both laser and non-coherent radiation sources. Either pulsed or continuous wave ("CW") lasers can be used, and the lasant medium can be gaseous, liquid or solid state. One preferred laser source is a pulsed excimer laser, such as a KrF laser. Alternatively, rare earth-doped solid state lasers, ruby lasers and Nd:YAG lasers can be operated in conjunction with frequency modification means to produce an output beam at the appropriate UV wavelength. In another alternative, a UV flash lamp can be employed.

The UV radiation source preferably produces an output beam having a wavelength less than about 280 nanometers. The therapeutic UV radiation useful in the present invention will typically range from about 280 nanometers down to about 240 nanometers (due to the limited transmission efficiency of glass fibers at lower wavelengths). In one preferred embodiment, a laser system is disclosed which operates at about 266 nanometers to maximize the cytotoxic effect of the radiation. Other useful UV radiation sources include, for example, Argon ion lasers emitting UV light at about 257 nanometers and KrF excimer lasers emitting light at about 248 nanometers.

The invention can be practiced with a low energy radiation source. The term "low energy" is used herein to describe both laser and non-coherent radiation systems having an energy output of less than about 5 millijoules.

Usage of a high energy pulsed UV radiation source may be preferred for some applications. The term "high energy" is used herein to describe lasers which have an energy output of more than 5 millijoules or which generate peak powers on the order of 100 kilowatts per square centimeter or greater.

In one embodiment of the invention, at least one optical fiber for transmission of UV radiation is incorporated into a conventional balloon angioplasty device and operated to deliver therapeutical UV radiation to the angioplasty site either at the same time the balloon is inflated, or shortly before or after inflation. In one preferred method, the balloon is first inflated to displace the vessel-obstructing plaque or lesion, and then the balloon is retracted to permit irradiation of the site by one or optical waveguides incorporated into the catheter. In one illustrated embodiment, the balloon catheter has a diffusive tip through which the therapeutic UV laser radiation of the invention is delivered.

In another embodiment of the invention, at least one optical waveguide for transmission of UV radiation can be incorporated into an laser angioplasty device as an adjunct to the delivery of ablative laser radiation. Thus, a single catheter preferably can carry two bundles of optical fibers, one bundle serving to deliver ablative radiation (e.g., from a high energy, pulsed, excimer laser) and the other bundle carrying the UV radiation to kill a portion of the cells in the vicinity of the ablation site which would otherwise proliferate.

In this embodiment, the ablative and therapeutic radiation can be provided by two or more lasers operating in tandem, one laser source being used to deliver ablative laser radiation, and another laser source then employed to inhibit restenosis. In one preferred embodiment, separate optical waveguides can be used to deliver the ablative and therapeutic laser radiation, and two controllers are provided, one for each laser source, to allow them to operate independently. Alternatively, the ablative and therapeutic radiation can multiplexed and delivered via the same waveguide. The ablative laser radiation source can be any form of laser deemed appropriate for the particular application involved. In another alternative, a tunable laser delivering radiation at two or more wavelengths can be used and may be preferred for particular applications.

In yet another embodiment of the invention, a single wavelength of UV laser radiation can be generated, and such radiation can also be used to ablate the vessel-obstructing plaque or other lesion as well as reduce restenosis. Thus, in this embodiment, UV radiation is transmitted through an optical waveguide to both perform angioplasty and kill smooth muscle cells at the angioplasty site.

In another aspect of the invention, novel UV radiation sources are disclosed herein. In one illustrated embodiment, a laser having an output beam wavelength of about 1064 nanometers, such as a common Nd:YAG laser, can be used in conjunction with two doubling crystals to yield a radiation output of about 266 nanometers and an energy output of about 5-10 millijoules. A grouping of six to eight fibers delivering such radiation can be used to provide the laser power necessary for both ablation of plaque and treatment of the site to reduce the likelihood of restenosis.

Novel catheter systems are also disclosed herein. Such catheter systems are useful in the performance of either balloon angioplasty or laser angioplasty and are preferably equipped with at least one optical waveguide for delivery of the UV radiation therapY, which can be, for example, an optical fiber having about a 200 micron diameter core. The catheter tip can also contain focusing optics or diffusive elements for use in directing the radiation emitted from the catheter within an artery.

The invention will next be described in connection with certain illustrated embodiments. However, it should be clear that various changes and modifications can be made by those skilled in the art without departing from the spirit or scope of the invention.

DETAILED DESCRIPTION

Figure 1:
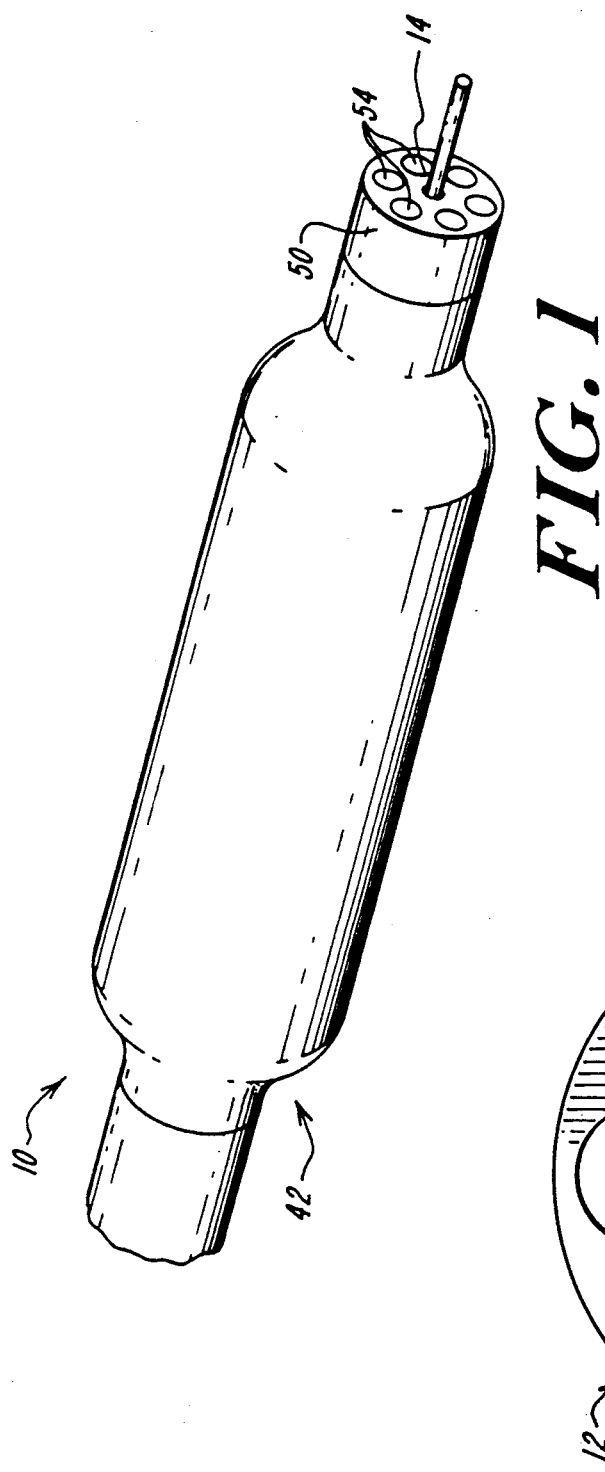
FIG. 1 is a schematic perspective view of a combined balloon and laser therapy catheter for performing angioplasty and reducing the likelihood of restenosis.
Figure 2:
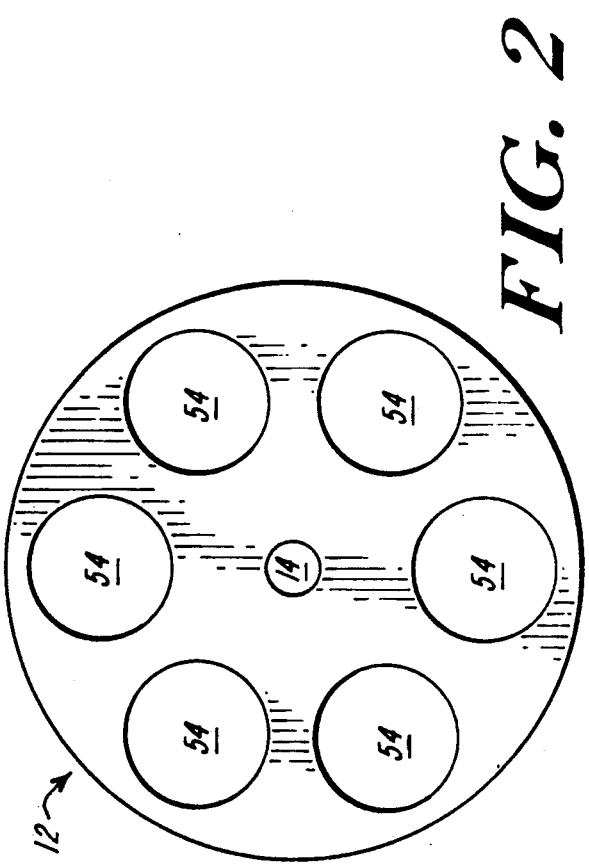
FIG. 2 is a view of the distal end of the catheter of FIG. 1.

In FIG. 1, a combined balloon and laser therapY catheter 10 is shown, including inflatable balloon section 42 and a guide wire 14. Also disposed within the catheter are a plurality of optical fibers 54 for delivery of ultraviolet radiation. The catheter can also include a radio-opaque tip 50. In FIG. 2, the distal end 12 of the catheter of FIG. 1 is shown in more detail, including an exemplary disposition of six optical fibers 54 about a central guide wire 14.

Figure 3A:
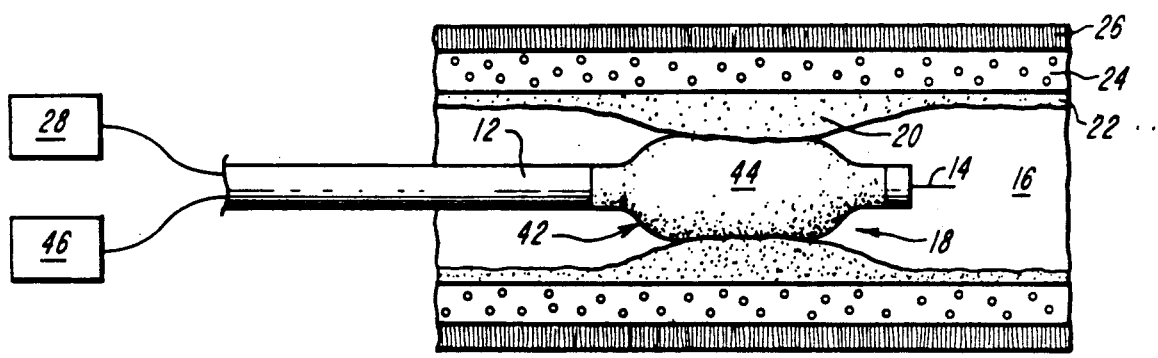
FIGS. 3A-3C are schematic cross-sectional illustrations of a system incorporating the catheter of FIG. 1 in use to dilate a blood vessel and prevent restenosis.
Figure 3B:
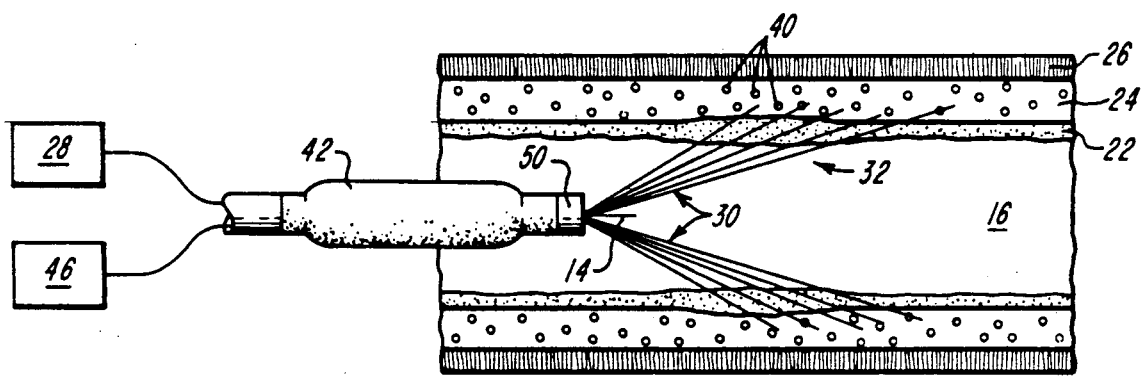
Figure 3C:
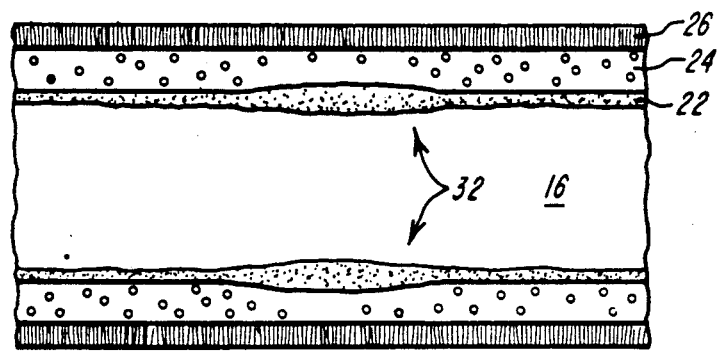

The use of the catheter system 10 is schematically illustrated in FIGS. 3A-3C. In use, the guide wire 14 is first introduced into the obstructed blood vessel and used to guide the catheter 10 into position adjacent to the plaque or lesion (e.g., under radiographic control). As shown in FIG. 3A, the balloon section 42 is then inflated to form a balloon 44 which applies pressure against the obstruction 20, thereby dilating the obstructed region of the blood vessel 16. Inflation and deflation of the balloon 44 are controlled by a balloon controller 46.

In FIG. 3B, the balloon section 42 is deflated and retracted so that the distal tip of the catheter can be positioned to deliver UV radiation therapy to the angioplasty site 32. A therapeutical laser 28 can then be activated to deliver UV radiation 30 which will kill a major portion of the smooth muscle cells 40 within the media 24 of the blood vessel wall without damaging either the inner endothelium layer 22 or the outer adventitia 26 of the blood vessel.

As shown in FIG. 3C, the end result of the operation is a substantially lessened obstruction with few, if any, smooth muscle cells remaining in the angioplasty site to proliferate and cause restenosis.

Figure 4:
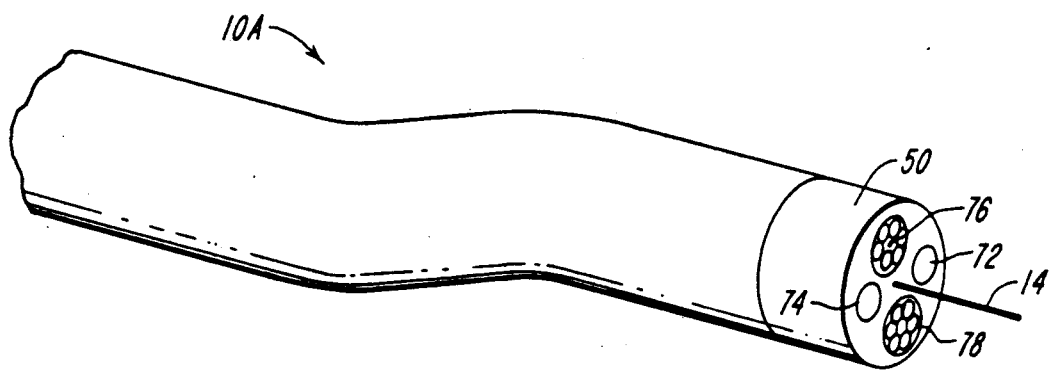
FIG. 4 is a schematic perspective view of an alternative catheter for performing angioplasty and reducing the likelihood of restenosis.
Figure 5:
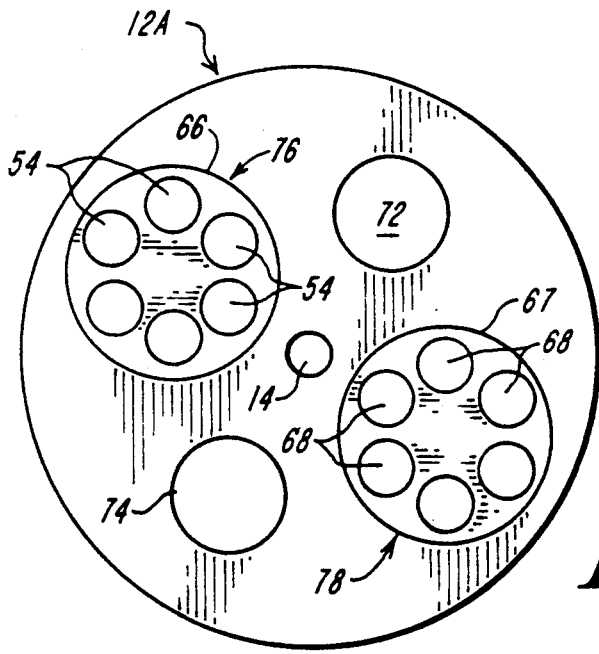
FIG. 5 is a view of the distal end of the catheter of FIG. 4.

In FIGS. 4 and 5, an alternative catheter configuration 10A for performing both angioplasty and reducing the likelihood of stenosis is shown, including a guide wire 14 and two laser radiation delivery systems 76 and 78. The first laser delivery system 76 provides therapeutic UV radiation to inhibit restenosis. The second laser delivery system 78 operates to provide ablative laser radiation to remove obstructions in a blood vessel by photodecomposition. Like the system of FIG. 1, the catheter of FIG. 4 can also include a radio-opaque tip 50 to aid in positioning the catheter within a blood vessel under radiographic control.

As shown in more detail in FIG. 5, the distal end of 12A of the catheter can include both the therapeutic UV radiation delivery system 76 and the ablative laser radiation delivery system 78. Multiple optical fibers 54 for UV radiation therapy are encased in a sleeve 66 which is positioned on one side of the guide wire to provide the UV therapy system. A second sleeve 67, encasing another set of optical fibers 68 for laser ablation, is positioned on the other side of the guide wire 14. The catheter can further include a flushing port 72 for the introduction of saline at the site and/or a suction port 74 for clearing the site of fluids during laser operations. The optical waveguides 68 may be of any type appropriate to deliver the ablative laser radiation required for a particular application. For example, the optical waveguide 68 can be optical fibers connected to an ablative radiation source such as a XeCl excimer laser operating in a pulsed mode at about 308 nanometers.

Figure 6A:
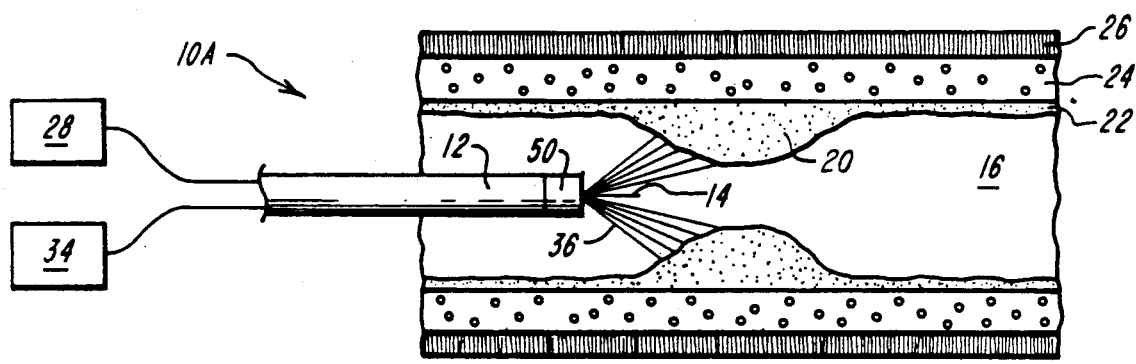
FIGS. 6A-6C are schematic cross-sectional illustrations of a system incorporating the catheter of FIG. 4 in use to dilate a blood vessel and prevent restenosis.
Figure 6B:
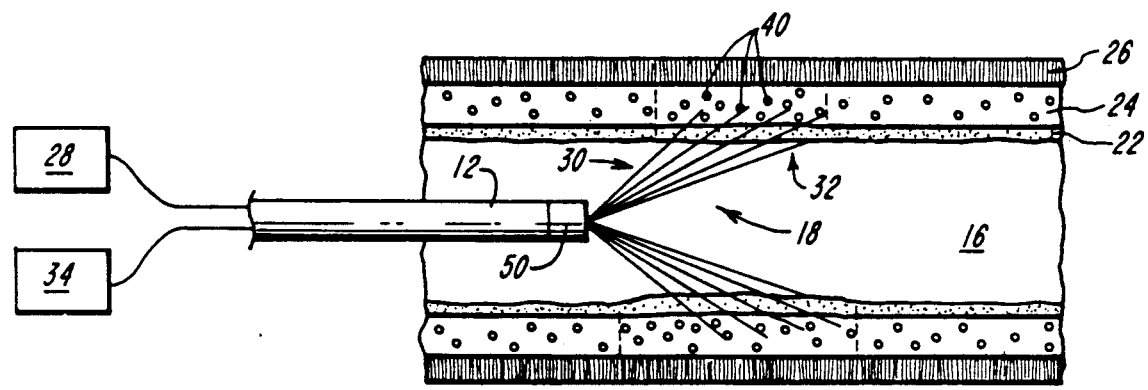
Figure 6C:
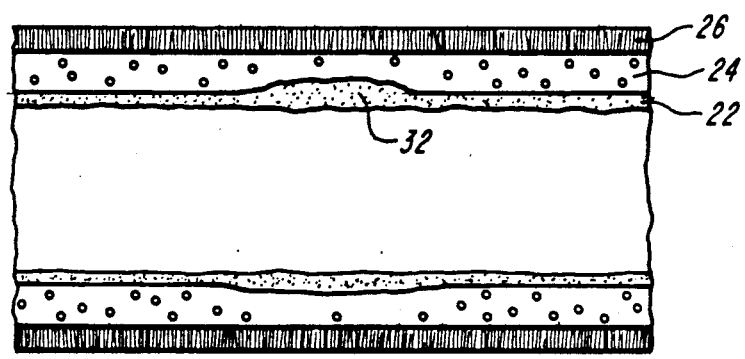

The use of the catheter system 10A is schematically illustrated in FIGS. 6A–6C. As shown, the catheter and guide wire can be introduced into a blood vessel 16. The walls of the blood vessels are characterized as having an inner endothelium layer 22, a media populated by smooth muscle cells 24 and an outer adventitia 26. In atherosclerotic disease, the endothelium 22 is interrupted by lesions of raised fibers plaque 20. In use, the catheter 10A is positioned next to the obstruction 20 and the ablative radiation source 3B is activated to provide a radiation beam 36 which removes the plaque by photodecomposition. Next, the therapeutic UV radiation source 28 is activated to provide a second beam of radiation 30 which is directed to the smooth muscle cells 40 within the blood vessel media 28 at the angioplasty site 32.

Following the therapeutic UV radiation, the catheter can be withdrawn as shown in FIG. 6C, and few smooth muscle cells will remain within the area of the angioplasty injury. By killing a major portion of the smooth muscle cells, the risk of restenosis is again decreased.

As noted above, the therapeutic UV radiation can be provided by a variety of sources, including non-coherent UV light sources and excimer laser sources (e.g., a KrF excimer laser operating at 248 nanometers).

Figure 7:
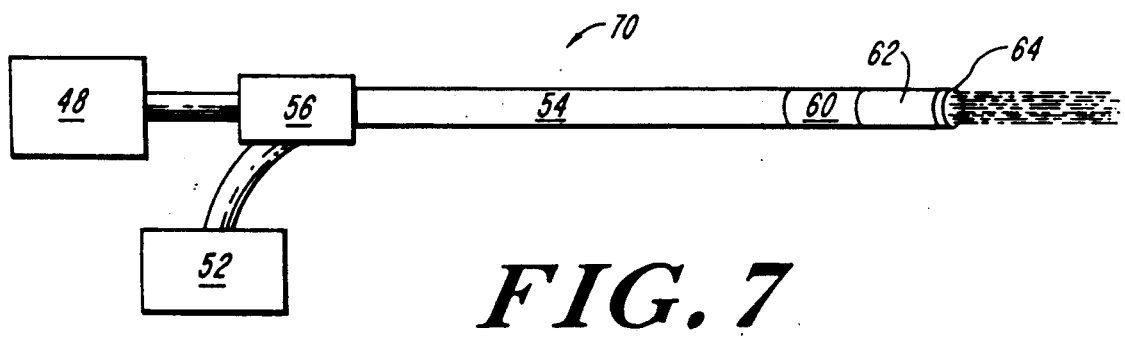
FIG. 7 is a schematic illustration of a laser device useful in the present invention.

In FIG. 7, an alternative laser device 70 is shown which can be used in the present invention to provide the therapeutic UV radiation. In the system 70, an output beam from a laser source 48, such as Nd:YAG laser with an output radiation having a wavelength of about 1064 nanometers is introduced via coupler 56 into an optical fiber 54 which is preferably a rare earth-doped silica fiber (e.g. a Neodymium-doped optical fiber). As the radiation from laser source 48 is introduced into the optical fiber 54, the fiber is also optically pumped by an optical pump source 52 (e.g., a laser diode having an output radiation wavelength of about 808 nanometers, likewise coupled to the fiber 54 by coupler 56). The doped optical fiber thus acts a laser amplifier.

At the distal end of fiber 54, the system is terminated in two frequency-multiplying crystals 60 and 62. The first crystal 60 is a frequency-doubling optical element, such as a potassium dihydrogen phosphate (KDP) crystal, and the second crystal 62 is also a frequency-doubling optical element, such as a barium boron oxide (BBO) crystal. Focusing optics 64, such as a grated refractive index ("GRIN") lens, can be included at the output end of the optical fiber 54. With the system as described, therapeutic laser radiation of a wavelength of about 266 nanometers is produced. Further details on the devices, such as that shown in FIG. 7, can be found in a copending, commonly-owned patent application entitled "Laser Therapy Instruments" filed on even date herewith and incorporated by reference.

The utility of UV radiation in reducing the proliferation of vascular smooth muscle cells has been further demonstrated by experiments. In one set of experiments using cultured cells, the A10 rat embryonic thoracic aorta cell line was obtained from the American Type Culture Collection. This clonal, smooth muscle line was derived from the thoracic aorta of DD1X embryonic rats. The cells possess many of the characteristics of end-stage smooth muscle cells; they produce spontaneous action potential at the stationery phase of growth and exhibit an increase in activity of the enzymes mykinase and creatine phosphokinase.

The cell line was propagated in DMEM medium supplemented with 10% fetal bovine serum and glutamine. These cells were plated on well tissue culture plates. After incubation for three to four days, cells in expotential growth were irradiated using laser radiation of various wavelengths. All of the experiments were run at a laser repetition rate of 10 Hz. The area of cell wall exposed was approximately 9.62 cm$^2$. The results are detailed in Table 1 below.

TABLE 1

| | Results of Laser Irradiation of Smooth Muscle Cells | | |
|---|---|---|---|
| Laser Wavelength | Energy/Pulse | Exposure Time | Surviving Fraction |
| control | — | — | 1.05 |
| control | — | — | 0.95 |
| 266 nm | 10 mj | 1 min | 0.00916 |
| 266 nm | 9.6 mj | 15 sec | 0.0358 |
| 266 nm | 9.9–1.1 mj | 1 min | 0.114 |
| 355 nm | 10.2 mj | 1 min | 1.12 |
| 1064 nm | >10 mj | 1 min | 1.03 |
| 266 + 532 + 1064 | >10 mj | 1 min | <0.001 |
| 532 + 1064 | >10 mj | 1 min | 1.08 |

These results clearly demonstrate the efficacy of UV radiation in killing aortic smooth muscle cells. Cell cultures exposed to as little as 15 seconds of UV radiation exhibited survival rates below 1 percent.

What we claim is:

1. A method of inhibiting restenosis associated with angioplasty, the method comprising:

disposing an optical waveguide means inside a blood vessel;

locating the waveguide means adjacent to an angioplasty side within the vessel; and irradiating the angioplasty site with UV radiation having a wavelength ranging from about 240 to about 280 nanometers via said optical means to deliver non-ablative, cytotoxic radiation to smooth muscle cells forming the blood vessel in the vicinity of the angioplasty side thereby reducing susceptibility to restenosis due to blood vessel cell proliferation.

2. The method of claim 1 wherein the step of irradiating the angioplasty site further includes irradiating with a laser radiation beam via the optical waveguide means having a wavelength of about 248 to about 268 nanometers.

3. The method of claim 1 wherein the step of disposing the waveguide means inside a blood vessel further comprises employing a catheter means to carry the waveguide means.

4. The method of claim 1 wherein the method further comprises delivering ablative radiation having sufficient energy to photodecompose blood vessel plaque via the optical waveguide means to remove plaque at the angioplasty site.

5. The method of claim 1 wherein the method further comprises disposing a second optical waveguide means inside the blood vessel for delivery of ablative laser radiation having sufficient energy to photodecompose blood vessel plaque at the angioplasty site.

6. The method of claim 1 wherein the method further comprises employing with said waveguide means an inflation means disposed within the blood vessel for dilation of said blood vessel to perform angioplasty.

* * * * *